US00PP20483P2

(12) United States Plant Patent
Eveleens

(10) Patent No.: US PP20,483 P2
(45) Date of Patent: Nov. 17, 2009

(54) ***HYDRANGEA* PLANT NAMED 'MAGICAL OPAL'**

(50) Latin Name: *Hydrangea macrophylla*
Varietal Denomination: Magical Opal

(75) Inventor: Cornelis Pieter Eveleens, De Kwakel (NL)

(73) Assignee: Kolster Beheer BV., Boskoop (NL)

( * ) Notice: Subject to any disclaimer, the term of this patent is extended or adjusted under 35 U.S.C. 154(b) by 0 days.

(21) Appl. No.: 12/221,689

(22) Filed: Aug. 4, 2008

(51) Int. Cl.
*A01H 5/00* (2006.01)

(52) U.S. Cl. ..... Plt./250

(58) Field of Classification Search ..... Plt./250
See application file for complete search history.

*Primary Examiner*—Kent L Bell
(74) *Attorney, Agent, or Firm*—C. A. Whealy

(57) ABSTRACT

A new and distinct cultivar of *Hydrangea* plant named 'Magical Opal', characterized by its upright and mounded plant habit; strong roots and stems; and large dense inflorescences with dark pink-colored flowers.

2 Drawing Sheets

Botanical designation: *Hydrangea macrophylla.*
Cultivar denomination: 'Magical Opal'.

BACKGROUND OF THE INVENTION

The present invention relates to a new and distinct cultivar of *Hydrangea,* botanically known as *Hydrangea macrophylla* and hereinafter referred to by the name 'Magical Opal'.

The new *Hydrangea* is a product of a planned breeding program conducted by the Inventor in Aalsmeer, The Netherlands. The objective of the breeding program was to create new *Hydrangea* cultivars with strong stems, large inflorescences and attractive flower color.

The new *Hydrangea* originated from a cross-pollination made by the Inventor in 2002 in Aalsmeer, The Netherlands, of two unnamed seedling selections of *Hydrangea macrophylla,* not patented. The new *Hydrangea* was discovered and selected by the Inventor as a single flowering plant within the progeny of the stated cross-pollination in a controlled greenhouse environment in Aalsmeer, The Netherlands in 2004.

Asexual reproduction of the new *Hydrangea* by vegetative cuttings in a controlled greenhouse environment in Aalsmeer, The Netherlands since 2004, has shown that the unique features of this new *Hydrangea* are stable and reproduced true to type in successive generations.

SUMMARY OF THE INVENTION

Plants of the new *Hydrangea* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Magical Opal'. These characteristics in combination distinguish 'Magical Opal' as a new and distinct cultivar of *Hydrangea:*

1. Upright and mounded plant habit.
2. Strong roots and stems.
3. Large and dense inflorescences with dark pink-colored flowers.

Plants of the new *Hydrangea* differ from plants of the parent selections primarily in plant habit as plants of the new

*Hydrangea* are more uniform than plants of the parent selections. In addition, plants of the new *Hydrangea* have larger flowers than plants of the parent selections.

Plants of the new *Hydrangea* can be compared to plants of *Hydrangea* 'Bodensee', not patented. Plants of the new *Hydrangea* differ from plants of 'Bodensee' in the following characteristics:

1. Plants of the new *Hydrangea* have denser inflorescences than plants of 'Bodensee'.
2. Plants of the new *Hydrangea* have sturdier and thicker flowers than plants of 'Bodensee'.

BRIEF DESCRIPTION OF THE PHOTOGRAPHS

The accompanying colored photographs illustrate the unique appearance of the new cultivar, showing the colors as true as it is reasonably possible to obtain in colored reproductions of this type. Colors in the photographs may differ from the color value cited in the detailed botanical description which accurately describe the colors of the new *Hydrangea.*

The photograph on the first sheet comprises a side perspective view of a typical flowering plant of 'Magical Opal' grown in a container.

The photograph at the top of the second sheet is a close-up view of a typical inflorescence of 'Magical Opal'.

The photograph at the bottom of the second sheet is a close-up view of a typical leaf of 'Magical Opal'.

DETAILED BOTANICAL DESCRIPTION

In the following description, color references are made to The Royal Horticultural Society Colour Chart, 2001 Edition, except where general terms of ordinary dictionary significance are used. Plants used in the aforementioned photographs and in the following description were grown during the spring in Boskoop, The Netherlands, in containers in a glass-covered greenhouse and under conditions which closely approximate commercial production conditions. During the production of the plants, day and night temperatures ranged from 17° C. to 19° C. Plants of the new *Hydrangea* were pinched one time and had been planted for two years when the photographs and description were taken.

Botanical description: *Hydrangea macrophylla* 'Magical Opal'.

Parentage:

*Female, or seed, parent.*—Unnamed seedling selection of *Hydrangea macrophylla,* not patented.

*Male, or pollen, parent.*—Unnamed seedling selection of *Hydrangea macrophylla,* not patented.

Propagation:

*Method.*—By cuttings.

*Time to initiate roots, summer.*—About 20 days at temperatures of 17° C. to 25° C.

*Time to initiate roots, winter.*—About 30 days at temperatures of 10° C. to 15° C.

*Time to produce a rooted young plant, summer.*—About 40 days at temperatures of 17° C. to 25° C.

*Time to produce a rooted young plant, winter.*—About 70 days at temperatures of 10° C. to 15° C.

*Root description.*—Medium in thickness, fibrous; creamy brown in color.

*Rooting habit.*—Freely branching; moderately dense.

Plant description:

*Form/growth habit.*—Upright and mounded plant habit; broad inverted triangle. Strong lateral branches; moderately vigorous growth habit.

*Plant height.*—About 50.9 cm.

*Plant diameter or area of spread.*—About 56.8 cm.

*Branching habit.*—Moderate branching with about five lateral branches per plant; pinching enhances lateral branch development.

*Lateral branches.*—Length: About 37.5 cm. Diameter: About 7 mm. Internode length: About 7.9 cm. Texture: Smooth, glabrous. Strength: Strong. Color: Close to 144A to 144B.

Foliage description:

*Arrangement.*—Opposite, simple.

*Length.*—About 14.3 cm.

*Width.*—About 10.9 cm.

*Shape.*—Broadly elliptic to broadly oval.

*Apex.*—Acute.

*Base.*—Rounded to attenuate.

*Margin.*—Serrate.

*Texture, upper and lower surfaces.*—Smooth, glabrous.

*Venation pattern.*—Pinnate.

*Color.*—Developing leaves, upper surface: Between 139A and 141A. Developing leaves, lower surface: Close to 138B. Fully expanded leaves, upper surface: Close to 137A; venation, close to 145B to 145C. Fully expanded leaves, lower surface: Close to 138B; venation, close to 145C.

*Petiole.*—Length: About 3 cm. Diameter: About 4 mm. Texture, upper and lower surfaces: Smooth, glabrous. Color, upper and lower surfaces: Close to 144B.

Flower description:

*Flower type and habit.*—Single fertile and sterile flowers arranged on terminal panicles; panicles large, flattened and globular. Flowers face upright to outward. Flowers not fragrant.

*Natural flowering season.*—Continuous flowering from early May until October in The Netherlands.

*Flower longevity.*—Flowers maintain good substance and color for about four weeks on the plant. Flowers persistent.

*Quantity of flowers.*—Freely flowering habit; about 90 fertile flowers and about 140 sterile flowers per panicle.

*Panicle height.*—About 10.9 cm.

*Panicle diameter.*—About 18.1 cm.

*Fertile flower diameter.*—About 8 mm.

*Fertile flower depth (height).*—About 3 mm.

*Sterile flower diameter.*—About 4.3 cm.

*Sterile flower depth (height).*—About 1.6 cm.

*Flower buds.*—Length: About 2 mm. Diameter: About 2.5 mm. Shape: Flattened globular. Color: Close to 73B.

*Petals, present on fertile flowers only.*—Arrangement: About three in a single whorl. Length: About 3 mm. Width: About 1.5 mm. Shape: Broadly ovate. Apex: Acute. Base: Attenuate. Margin: Entire. Texture, upper and lower surfaces: Smooth, glabrous. Color: When opening and fully opened, upper surface: Close to 75B to 75C. When opening and fully opened, lower surface: Close to 75B.

*Sepals, fertile flowers.*—Quantity per flower: About five in a single whorl. Length: About 2 mm. Width: About 1 cm. Shape: Ovate. Apex: Acute. Base: Cuneate. Margin: Entire. Texture, upper and lower surfaces: Smooth, glabrous. Color, immature, upper and lower surfaces: Close to N155B to N155C. Color, mature, upper and lower surfaces: Close to N155B to N155C.

*Sepals, sterile flowers.*—Quantity per flower: About four in a single whorl. Length: About 2.2 cm. Width: About 2.5 cm. Shape: Broadly deltoid to orbicular. Apex: Rounded to bluntly acute. Base: Cuneate. Margin: Entire. Texture, upper and lower surfaces: Smooth, glabrous. Color, immature, upper surface: Close to 64C. Color, immature, lower surface: Close to 73B to 73C. Color, mature, upper surface: Close to 68A. Color, mature, lower surface: Close to 73B to 73C.

*Pedicels, fertile flowers.*—Angle: About 10° from vertical. Strength: Moderately strong. Length: About 4.5 mm. Diameter: About 1 mm. Texture: Smooth, glabrous. Color: Close to 65A to 65B.

*Pedicels, sterile flowers.*—Angle: About 45° from vertical. Strength: Moderately strong. Length: About 2.8 cm. Diameter: About 1.5 mm. Texture: Smooth, glabrous. Color: Close to 65A.

*Reproductive organs, present on fertile flowers only.*—Stamens: Quantity per flower: About ten. Filament length: About 4 mm. Filament color: Close to 155C. Anther shape: Reniform. Anther length: About 0.8 mm. Anther color: Close to 197C to 197D. Pollen amount: Scarce. Pollen color: Close to 156D. Pistils: Pistil quantity per flower: About three. Pistil length: About 2 mm. Stigma shape: Club-shaped. Stigma color: Close to N155A. Style length: About 1.5 mm. Style color: Close to N155A. Ovary color: Close to N155C.

*Fruits/seeds.*—Fruit and seed development have not been observed on plants of the new *Hydrangea.*

Disease/pest resistance: Plants of the new *Hydrangea* have been observed to be relatively resistant to Powdery Mildew; plants of the new *Hydrangea* have not been observed to be resistant to pests or other pathogens common to *Hydrangea.*

Temperature tolerance: Plants of the new *Hydrangea* have been shown to be tolerant to temperatures ranging from about −15° C. to about 30° C.

It is claimed:

1. A new and distinct *Hydrangea* plant named 'Magical Opal' as illustrated and described.

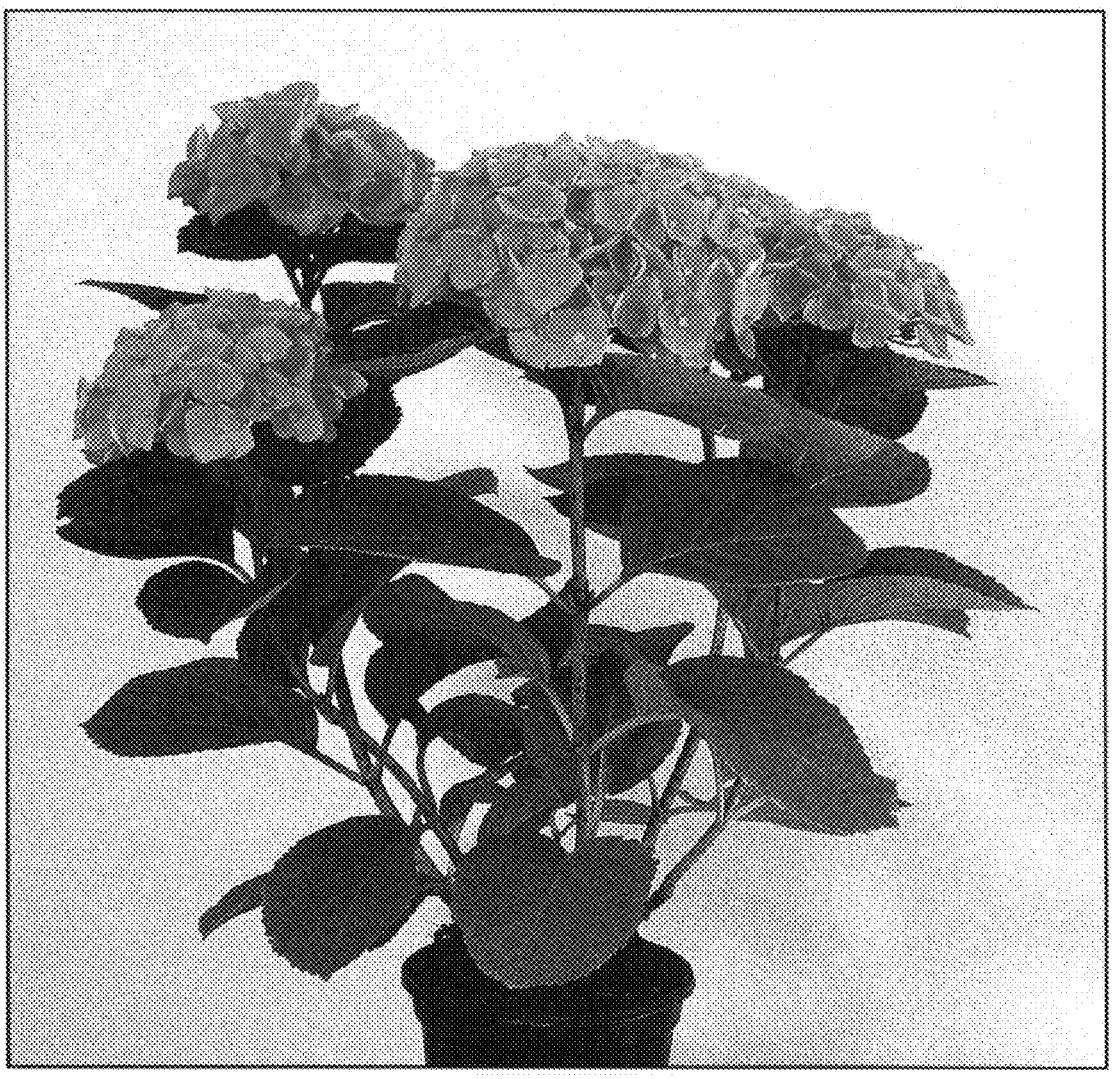

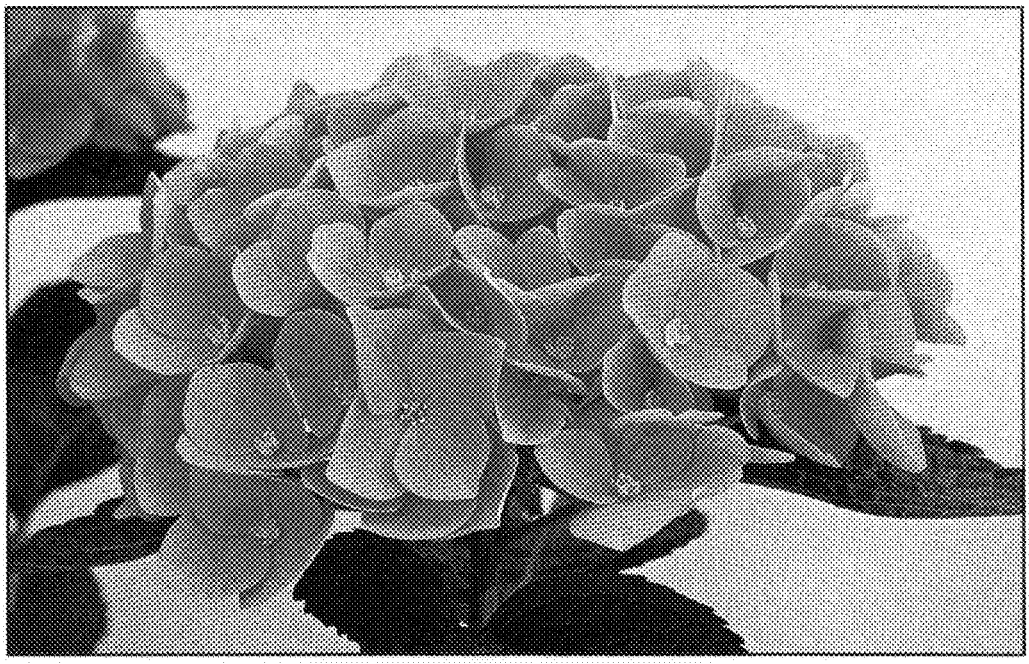
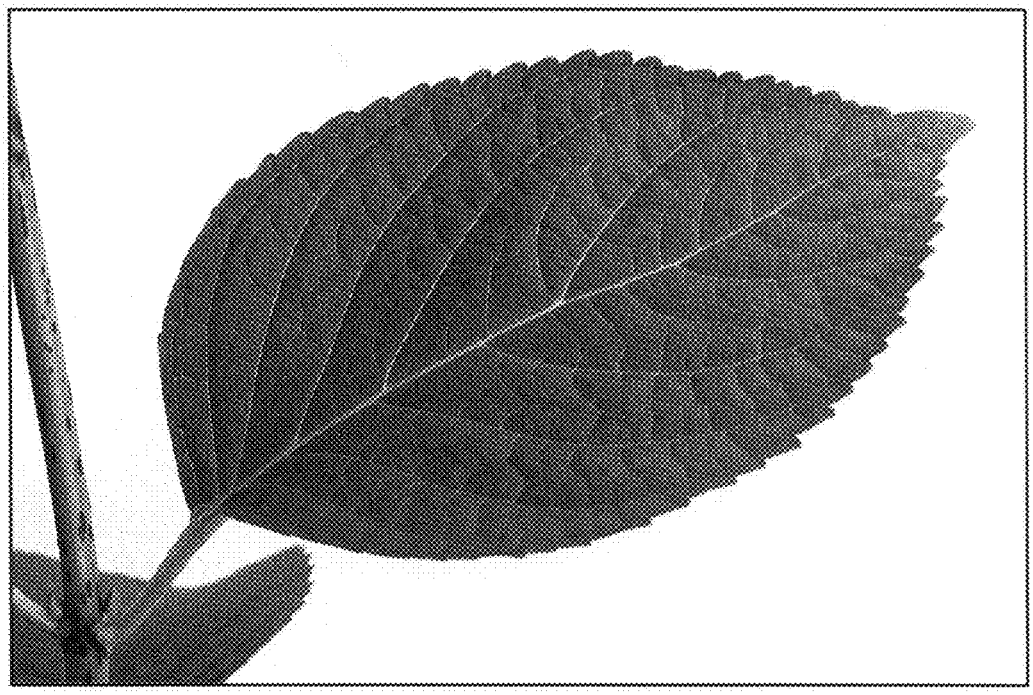

* * * * *